United States Patent [19]

Diehr et al.

[11] Patent Number: 4,769,455
[45] Date of Patent: Sep. 6, 1988

[54] BENZODISULTAMS

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 13,611

[22] Filed: Feb. 12, 1987

Related U.S. Application Data

[62] Division of Ser. No. 769,191, Aug. 23, 1985.

[30] Foreign Application Priority Data

Aug. 30, 1984 [DE] Fed. Rep. of Germany ....... 3431922
May 9, 1985 [DE] Fed. Rep. of Germany ....... 3516616

[51] Int. Cl.[4] .................. C07D 285/36; C07D 285/38
[52] U.S. Cl. ..................................... 540/545; 540/552
[58] Field of Search ................................ 540/552, 545

[56] References Cited

U.S. PATENT DOCUMENTS

| | | | |
|---|---|---|---|
| 3,313,811 | 4/1967 | Becke | 544/5 |
| 3,803,149 | 4/1974 | Malen et al. | 540/549 |
| 3,974,155 | 8/1976 | Cross et al. | 540/552 |

OTHER PUBLICATIONS

Merck et al., Rahway, N.J., 1977, P. Organic Nance Reactors-44.

Gorki, Abstract SU 1109-396-A, 8/23/84.
Desulfurization with Raney Nickel, II, Sulfonamides[1,2], George R. Pettit and Raymond E. Kadunce, vol. 27, (Dec. 1962), pp. 4566-4570.
J. Org. Chem., vol. 39, No. 24 (1974), DeChristopher, Adamek, Lyon, Klein, and Baumgauten, pp. 3525-3532.
Hendrickson et al., "o-Benzenedisulfonimide and Its Derivatives", J. Org. Chem., vol. 34, No. 11, (Nov. 1969), pp. 3434-3438.

*Primary Examiner*—John M. Ford
*Assistant Examiner*—J. G. Mullins
*Attorney, Agent, or Firm*—Sprung Horn Kramer & Woods

[57] ABSTRACT

The invention relates to new benzodisultams of the general formula (I)

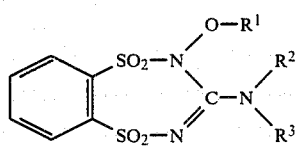

in which
$R^1$ represents an optionally substituted radical from the series comprising alkyl, alkenyl, alkinyl, cycloalkyl, cycloalkylalkyl, aralkyl and aryl,
$R^2$ represents hydrogen or an optionally substituted radical from the series comprising alkyl, alkenyl, alkinyl and aralkyl, and
$R^3$ represents an optionally substituted and/or optionally fused six-membered aromatic heterocyclic radical which contains at least one nitrogen atom, a process for their preparation and their use as herbicides.

1 Claim, No Drawings

BENZODISULTAMS

This is a division of application Ser. No. 769,191, filed 8/23/85.

The invention relates to novel benzodisultams, which form a new class of substance, an inventive process for their preparation and their use as herbicides.

Benzodisultams were not hitherto known from the literature. The use of similar compounds as herbicides was likewise not hitherto known.

New benzodisultams of the general formula (I)

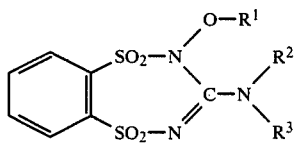

in which
  $R^1$ represents an optionally substituted radical from the series comprising alkyl, alkenyl, alkinyl, cycloalkyl, cycloalkylalkyl, aralkyl and aryl,
  $R^2$ represents hydrogen, or represents an optionally substituted radical from the series comprising alkyl, alkenyl, alkinyl and aralkyl and
  $R^3$ represents an optionally substituted and/or optionally fused six-membered aromatic heterocyclic radical, which contains at least one nitrogen atom,
have now been found.

The new compounds of the formula (I) are obtained by a process in which benzene-1,2-disulphonic acid dichloride of the formula (II)

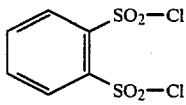

is reacted with oxyguanidine derivatives of the formula (III)

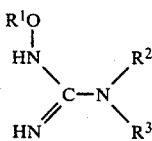

in which
  $R^1$, $R^2$ and $R^3$ have the abovementioned meanings,
in the presence of acid acceptors and if appropriate in the presence of diluents.

The new benzodisultams of the formula (I) are distinguished by a powerful herbicidal activity.

Surprisingly, the new compounds of the formula (I) exhibit a considerably more powerful herbicidal action than many known chemical compounds of the same type of action.

The invention preferably relates to compounds of the formula (I)
in which
  $R^1$ represents $C_1$–$C_{12}$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-amino-carbonyl], or represents $C_3$–$C_6$-alkenyl [which is optionally substituted by fluorine, chlorine or bromine], or represents $C_3$–$C_6$-alkinyl, $C_3$–$C_6$-cycloalkyl, $C_3$–$C_6$-cycloalkyl-$C_1$–$C_2$-alkyl or phenyl-$C_1$–$C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl], or represents phenyl [which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxycarbonyl],
and in which, furthermore,
  $R^2$ represents hydrogen, $C_1$–$C_4$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-aminocarbonyl], or represents $C_3$–$C_6$-alkenyl, $C_3$–$C_6$-alkinyl or phenyl-$C_1$–$C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl],
and in which, furthermore,
  $R^3$ represents the radical

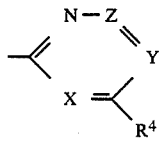

wherein
  $R^4$ represents hydrogen, fluorine, chlorine, bromine, hydroxyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], amino, $C_1$–$C_4$-alkylamino or di-($C_1$–$C_4$-alkyl)-amino,
  X represents nitrogen or a methine bridge (CH),
  Y represents nitrogen or an optionally substituted methine bridge C-$R^5$,
wherein
  $R^5$ represents hydrogen, fluorine, chlorine, bromine, $C_1$–$C_4$-alkyl, $C_1$–$C_4$-alkylcarbonyl or $C_1$–$C_4$-alkoxycarbonyl, and
  Z represents nitrogen, or an optionally substituted methine bridge C-$R^6$,
wherein
  $R^6$ represents hydrogen, fluorine, chlorine, bromine, hydroxyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], amino, $C_1$–$C_4$-alkylamino or di-($C_1$–$C_4$-alkyl)-amino.

The invention particularly relates to compounds of the formula (I)
in which
  $R^1$ represents $C_1$–$C_8$-alkyl [which is optionally substituted by fluorine or chlorine], $C_3$–$C_4$-alkenyl, $C_1$–$C_2$-alkoxy-carbonylmethyl, phenyl, phenethylor benzyl [which is optionally substituted by fluorine, chlorine, nitro, cyano, methyl, methoxy or methoxy-carbonyl],
  $R^2$ represents hydrogen and $R^3$ represents the radical

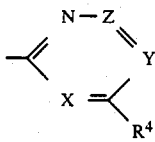

wherein
$R^4$ represents chlorine, methyl, ethyl, methoxy, ethoxy, methylthio or difluoromethoxy,
X represents nitrogen,
Y represents a methine bridge (CH) and
Z represents an optionally substituted methine bridge $C$-$R^6$,
wherein
$R^6$ represents hydrogen, chlorine, methyl, methoxy, ethoxy, methylthio, ethylthio, dimethylamino or diethylamino.

If, for example, N'-(4,6-dimethyl-pyrimidin-2-yl)-N''-allyloxy-guanidine and benzene-1,2-disulphonic acid dichloride are used as starting substances in the process according to the invention, the course of the reaction can be outlined by the following equation:

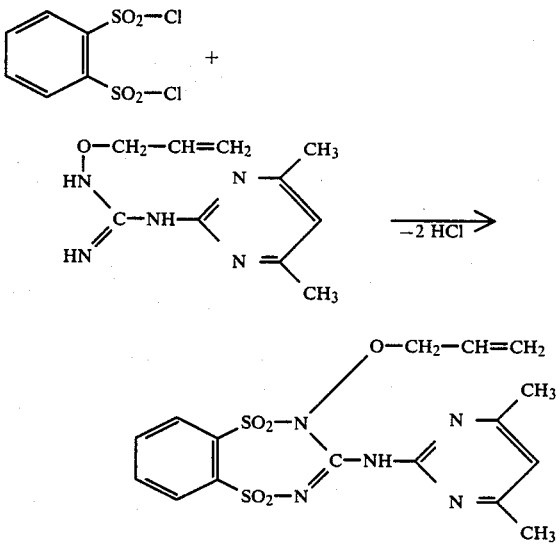

The benzene-1,2-disulphonic acid dichloride of the formula (II) to be used as the starting substance in the process according to the invention is already known (compare J. Org. Chem. 31 (1966), 3289–3292).

The oxyguanidine derivatives furthermore to be used as starting materials in the process according to the invention are generally defined in formula (III). In formula (III), $R^1$, $R^2$ and $R^3$ preferably and particularly have the same meanings as are given above as preferred or as particularly preferred in the context of the definition of the substituents of formula (I).

Examples which may be mentioned of starting substances of the formula (III) are: N'-(4-methyl-pyrimidin-2-yl)-, N'-(4,6-dimethyl-pyrimidin-2-yl)-, N'-(4-methoxy-6-methyl-pyrimidin-2-yl)-, N'-(4-ethyl-pyrimidin-2-yl)-, N'-(4-ethoxy-6-methyl-pyrimidin-2-yl)-, N'-(4-chloro-6-methoxy-pyrimidin-2-yl)-, N'-(4-chloro-6-ethoxy-pyrimidin-2-yl)-, N'-(4-chloro-6-dimethylamino-pyrimidin-2-yl)-, N'-(4-methyl-6-methylthio-pyrimidin-2-yl)-, N'-(4-dimethylamino-6-methyl-pyrimidin-2-yl)-, N'-(4,6-dimethoxy-pyrimidin-2-yl)-, N'-(4-difluoromethoxy-6-methyl-pyrimidin-2-yl)-, N'-(2,6-dimethyl-pyrimidin-4yl)- and N'-(2,6-dimethoxy-pyrimidin-4-yl)-N''-methoxy-guanidine, -N'''-ethoxy-guanidine, -N'''-propoxy-guanidine, -N'''-isopropoxy-guanidine, -N'''-butoxy-guanidine, -N'''-isobutoxy-guanidine, -N'''-sec.-butoxy-guanidine, -N'''-pentoxy-guanidine, -N'''-isopentoxy-guanidine, -N'''-hexyloxy-guanidine, -N'''-octyloxy-guanidine, -N'''-allyloxy-guanidine, -N'''-(2-chloro-ethoxy)-guanidine, -N'''-(2-fluoroethoxy)-guanidine, -N'''-(2-chloro-propoxy)-guanidine, -N''-(2-fluoro-propoxy)-guanidine, -N''-(3-chloro-propoxy)-guanidine, -N''-(4-chloro-butoxy)-guanidine, -N--methoxycarbonylmethoxy-guanidine, -N'''-ethoxy-carbonylmethoxy-guanidine, -N'''-(1-methoxy-carbonyl-ethoxy)-guanidine, -N'''-(1-ethoxycarbonyl-ethoxy)-guanidine, -N'''-(dimethylamino-carbonylmethoxy Oguanidine, -N'''-(2-phenyl-ethoxy)-guanidine, -N'''-phenoxy-guanidine, -N'''-(4-methyl-benzyloxy)-guanidine, -N'''-(4-fluoro-benzyloxy)-guanidine, -N'''-(4-chlorobenzyloxy)-guanidine, -N'''-(4-nitro-benzyloxy)-guanidine, -N'''-(2,6-dichloro-benzyloxy)-guanidine, -N'''-(4-methoxycarbonyl-benzyloxy)-guanidine and -N'''-(4-ethoxycarbonylbenzyloxy)-guanidine.

The starting substances of the formula (III) are known in some cases (compare J. Chem. Soc. 1962, 3915 and EP-A No. 121,082).

The compounds of the formula (III) are obtained by a process in which cyanamide derivatives of the formula (IV)

in which
$R^2$ and $R^3$ have the abovementioned meanings, are reacted with hydroxylamine derivatives of the formula (V)

in which
$R^1$ has the abovementioned meaning, or with hydrochlorides thereof, if appropriate in the presence of diluents, such as, for example, ethanol, propanol or butanol, at temperatures between 20° C. and 120° C., and, if appropriate, the reaction products are treated with acid acceptors, such as, for example, ammonia, potassium carbonate or sodium hydroxide.

The cyanamide derivatives of the formula (IV) are known in some cases (compare J. Chem. Soc. 1953, 1725). The compounds of the formula (IV) are essentially obtained by the following synthesis routes:

(a) by reaction of alkali metal or alkaline earth metal salts of cyanamide—such as, for example, sodium cyanamide or calcium cyanamide—with chloro-hetarenes of the formula (VI)

in which
$R^3$ has the abovementioned meaning,
and if appropriate—if $R^2$ does not represent hydrogen—subsequent reaction with halogen compounds of the formula (VII)

Q—R² (VII)

in which
R² represents an optionally substituted radical from the series comprising alkyl, alkenyl, alkinyl and aralkyl, and
Q represents chlorine, bromine or iodine,
if appropriate in the presence of inert diluents, such as, for example, acetone, acetonitrile or dimethylformamide, at temperatures between 0° C. and 100° C.

After the mixture has been concentrated and the residue has been dissolved in water, the cyanamide derivatives of the formula (IV) can be precipitated by acidification, for example with hydrochloric acid, and isolated by filtration with suction.

Alternatively, the compounds of the formula (IV) are obtained (b) in the case where R³ represents a substituted pyrimidinyl radical, by reaction of cyanoguanidine ("dicyandiamide") with β-dicarbonyl compounds or derivatives thereof, such as, for example, acetylacetone (compare J. Chem. Soc. 1953, 1725–1730), acetoacetic acid esters (compare J. Prakt. Chem. 77 (1908), 542 and J. Chem. Soc. 1948, 586) or malonic acid esters (compare German Patent Specification No. 158,591).

The 2-cyanoamino-4-hydroxy-6-methyl- or -4,6-dihydroxy-pyrimidines obtained from acetoacetic acid esters or malonic acid esters can be converted into the corresponding 2-cyanoamino-4-alkoxy-6-methyl- or -4,6-dialkoxy-pyrimidines in a known manner by reaction with alkylating agents, such as, for example, dimethyl sulphate or diethyl sulphate, if appropriate in the presence of diluents, such as, for example, water, methanol, ethanol, n- or iso-propanol, acetone, dioxane or dimethylformamide, and in the presence of acid-binding agents, such as, for example, sodium hydroxide, potassium hydroxide, sodium carbonate or potassium carbonate. To avoid N-alkylation, if necessary, acylation is carried out with an acylating agent, such as, for example, acetic anhydride or acetyl chloride, and, after the alkylation, the product is deacylated again with aqueous acids or bases.

In another alternative process, the compounds of the formula (IV) are obtained by a procedure in which (c) amino-hetarenes of the formula (VIII)

H₂N—R³ (VIII)

in which
R³ has the abovementioned meaning,
are reacted with carbonyl isothiocyanates of the formula (IX)

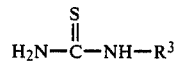

in which
R⁷ represents ethoxy or phenyl,
if appropriate in the presence of an inert diluent, such as, for example, acetone, acetonitrile or toluene, at temperatures between 0° C. and 100° C., the carbonylthioureas thereby formed, of the formula (X)

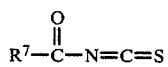

in which

R³ and R⁷ have the abovementioned meanings,
are isolated by filtration with suction, if appropriate after concentration of the mixture, and are reacted with aqueous alkali metal or alkaline earth metal hydroxide solutions, such as, for example, sodium hydroxide solution, if appropriate in the presence of an organic solvent, such as, for example, tetrahydrofuran or dioxane, at temperatures between 0° C. and 120° C., and the thioureas obtained after acidification, for example with hydrochloric acid, of the formula (XI)

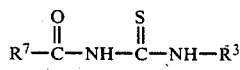

in which
R³ has the abovementioned meaning,
are isolated by filtration with suction and reacted with metal compounds which can bind hydrogen sulphide, such as, for example, with lead-II acetate, copper-II acetate, mercury-II acetate or iron-II acetate, in the presence of aqueous alkali metal or alkaline earth metal hydroxide solutions, such as, for example, sodium hydroxide solution, at temperatures between 20° C. and 100° C., the mixture is filtered, when the reaction has ended, and the filtrate is acidified with an acid, such as, for example, acetic acid. The products of the formula (IV) thereby obtained as crystals can be isolated by filtration with suction.

The starting substances for the preparation processes described above under (a), (b) and (c) for the cyanamide derivatives of the formula (IV) are known and/or can be prepared by processes which are known per se.

These starting substances include the chlorohetarenes of the formula (VI) (compare J. Chem. Soc. (C) 1966, 2031; Chem. Pharm. Bull. 11 (1963), 1382–1388 and Arch. Pharm. 295 (1962), 649–657), the halogen compounds of the formula (VII) (commercially available chemicals), the amino-hetarenes of the formula (VIII) (compare Chem. Pharm. Bull. 11 (1963), 1382–1388; J. Chem. Soc. 1946, 81 and U.S. Pat. No. 4,299,960) and the carbonyl isothiocyanates of the formula (IX) (compare J. Heterocycl. Chem. 5 (1968), 837 and U.S. Pat. No. 4,160,037).

The process according to the invention for the preparation of the new compounds of the formula (I) is preferably carried out using diluents. Possible diluents are virtually all the inert organic solvents, but preferably aprotic polar solvents. These include optionally halogenated hydrocarbons, such as, for example, methylene chloride, chloroform, toluene and chlorobenzene, nitriles, such as, for example, acetonitrile and propionitrile, dimethylformamide, dimethylacetamide, dimethylsulphoxide, sulpholane, hexamethylphosphoric acid triamide, 1,2-dimethoxyethane, pyridine and 2-methyl-5-ethyl-pyridine.

Virtually all the acid-binding agents which are usually employed can be used as acid acceptors in the process according to the invention. These include, in particular, alkali metal and alkaline earth metal hydrides, organometallic compounds, such as butyl-lithium, and furthermore aliphatic, aromatic or heterocyclic amines, such as trimethylamine, triethylamine, N,N-dimethylaniline, N,N-dimethyl-benzylamine, diazabicyclooctane (DABCO), diazabicycloundecene (DBU), pyridine, 2-methyl-5-ethyl-pyridine and 4-dimethylamino-pyridine.

The reaction temperatures can be varied within a substantial range in the process according to the invention. In general, the reaction is carried out between −80° C. and +100° C., preferably between −40° C. and +50° C. The process according to the invention is in general carried out under normal pressure.

For carrying out the process according to the invention, in general between 1.0 and 1.5 moles, preferably between 1.0 and 1.2 moles, of benzene-1,2-disulphonic acid dichloride of the formula (II) are employed per mole of oxyguanidine derivative of the formula (III). The reaction components are usually brought together at room temperature or with external cooling, and the reaction mixture is stirred until the reaction has ended.

The new compounds of the formula (I) can be worked up and isolated by customary methods. For example, the reaction mixture—if appropriate after dilution with a solvent which is virtually water-immiscible, such as, for example, methylene chloride—is washed with dilute hydrochloric acid and with water, dried, filtered and concentrated. The product of the formula (I), which remains in the residue, is made to crystallise by trituration with a suitable organic solvent, such as, for example, ethanol, and isolated by filtration with suction.

The active compounds according to the invention influence plant growth and can therefore be used as defoliants, desiccants, agents for destroying broad-leaved plants, germination inhibitors and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are suitable for combating monocotyledon and dicotyledon weeds in monocotyledon and dicotyledon cultures by the pre-emergence method and the post-emergence method. Control of germinating, emerging and already established weeds in perennial cultures, as well as total combating of vegetation on uncultivated land, is also possible.

The active compounds can be converted to the customary formulations, such as solutions, emulsions, suspensions, powders, foams, pastes, granules, aerosols, natural and synthetic materials impregnated with active compound, very fine capsules in polymeric substances, and in coating compositions for seed, and also formulations used with burning equipment, such as fumigating cartridges, fumigating cans, fumigating coils and the like, and ULV cold and warm moist formulations.

These formulations are produced in known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

For the mixtures come known herbicides, such as, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5-(4H)-one, 4-amino-6-(1,1-dimethylethyl)-3-ethylthio-1,2,4-triazin-5-(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5-(4H)-one, 2-chloro-4-ethylamino-6-isopropylamino-1,3,5-triazine, the R-enantiomer of (trimethylsilyl)-methyl 2-[4-(3,5-dichloro-pyridyl-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichlorophenoxy)-propionic acid, 4-chloro-2-methylphenoxy-acetic acid, 2-(2-methyl-4-chlorophenoxy)-propionic acid 3,5-diiodo-4-hydroxy-benzonitrile, 3,5-dibromo-4-hydroxy-benzonitrile and diphenyl ethers and phenylpyridazines, such as, for example, pyridates. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 15 kg of active compound per hectare of soil surface, preferably between 0.005 and 10 kg per ha.

The preparation and use of the active compounds according to the invention can be seen from the following examples.

PREPARATION EXAMPLES

Example 1

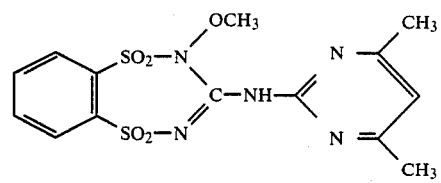

14 g (0.05 mole) of benzene-1,2-disulphonic acid dichloride are added in portions to a mixture of 10 g (0.05 mole) of N'-(4,6-dimethylpyrimidin-2-yl)-N''-methoxyguanidine, 12 g (0.15 mole) of pyridine and 100 ml of methylene chloride at −20° C. The mixture is subsequently stirred at −20° C. for 3 hours and at +20° C. for 15 hours. The reaction mixture is then washed with ice-cooled dilute hydrochloric acid and ice-water. The methylene chloride solution is dried and concentrated. The residue is triturated with ethanol. The residue thereby obtained as crystals is isolated by filtration with suction.

11.5 g (58% of theory) of the compound of the above-mentioned structural formula of melting point 158° C. (decomposition) are obtained.

The reaction mixture can also be worked up by a process in which, when the reaction has ended, the mixture is evaporated completely, the residue is taken up in dioxane, the mixture is filtered, the filtrate is evaporated again and the residue is recrystallised.

The compounds of the formula (I) listed in the following Table 1 can be prepared by the process described by way of example in the preceding example:

TABLE 1

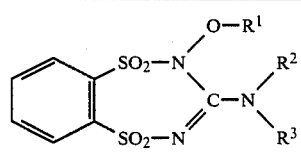
(I)

| Example No. | R¹ | R² | R³ | Melting point [°C.] |
|---|---|---|---|---|
| 2 | —C₂H₅ | H | 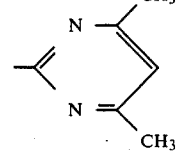 | 104 |

TABLE 1-continued $$\text{(I)}$$

Structure: benzene-1,2-disulfonyl with SO$_2$–N(O–R$^1$)–C(=N–SO$_2$)–N(R$^2$)(R$^3$)

| Example No. | R$^1$ | R$^2$ | R$^3$ | Melting point [°C.] |
|---|---|---|---|---|
| 3 | —C$_3$H$_7$(—i) | H | 4,6-dimethylpyrimidin-2-yl | (amorphous) |
| 4 | —C$_3$H$_7$(—n) | H | 4,6-dimethylpyrimidin-2-yl | 134 (amorphous) |
| 5 | —C$_4$H$_9$(—n) | H | 4,6-dimethylpyrimidin-2-yl | 179 (decomposition) |
| 6 | —C$_8$H$_{17}$(—n) | H | 4,6-dimethylpyrimidin-2-yl | 164 |
| 7 | —CH$_2$—C$_6$H$_5$ | H | 4,6-dimethylpyrimidin-2-yl | 198 |
| 8 | —CH$_2$CH$_2$—C$_6$H$_5$ | H | 4,6-dimethylpyrimidin-2-yl | |
| 9 | —CH$_2$COOC$_2$H$_5$ | H | 4,6-dimethylpyrimidin-2-yl | 210 (decompostion) |
| 10 | —C$_4$H$_9$(—i) | H | 4,6-dimethylpyrimidin-2-yl | |

TABLE 1-continued $$\text{(I)}$$

Structure (I): benzene-1,2-disulfonyl group with two N atoms; one N bears O-R¹, connected to C which has =N (to other sulfonyl N) and -N(R²)(R³).

| Example No. | R¹ | R² | R³ | Melting point [°C.] |
|---|---|---|---|---|
| 11 | —C₄H₉(—sec.) | H | 4,6-dimethylpyrimidin-2-yl | |
| 12 | —CH₂—C₆H₄—NO₂ (p) | H | 4,6-dimethylpyrimidin-2-yl | |
| 13 | —CH₂—C₆H₄—COOC₂H₅ (p) | H | 4,6-dimethylpyrimidin-2-yl | |
| 14 | —CH₂—C₆H₄—F (o) | H | 4,6-dimethylpyrimidin-2-yl | |
| 15 | —CH₂—C₆H₄—CH₃ (p) | H | 4,6-dimethylpyrimidin-2-yl | |
| 16 | —CH₂—C₆H₃—Cl₂ (2,6) | H | 4,6-dimethylpyrimidin-2-yl | |
| 17 | —CH₃ | —CH₃ | 4,6-dimethylpyrimidin-2-yl | |

TABLE 1-continued $$\text{(I)}$$

Structure: benzene ring with two $SO_2$ groups; one $SO_2-N(O-R^1)$ connected to $C(=N-SO_2)$ which bears $N(R^2)(R^3)$.

| Example No. | $R^1$ | $R^2$ | $R^3$ | Melting point [°C.] |
|---|---|---|---|---|
| 18 | $-CH_2-CH=CH_2$ | H | pyrimidine with 4,6-di-$CH_3$ | 180 |
| 19 | $-CH_3$ | H | pyrimidine with 4-$CH_3$ | |
| 20 | $-C_2H_5$ | H | pyrimidine with 4-$C_2H_5$ | |
| 21 | $-CH_3$ | H | pyridine with 2,4-di-$CH_3$ | |
| 22 | $-CH_3$ | H | pyrimidine with 4-$OCHF_2$, 6-$CH_3$ | |
| 23 | $-CH_3$ | H | pyrimidine with 4,6-di-$OCH_3$ | |
| 24 | $-C_4H_9(-sec.)$ | H | pyrimidine with 4,6-di-$OCH_3$ | |
| 25 | $-C_4H_9(-i)$ | H | pyrimidine with 4,6-di-$OCH_3$ | |

TABLE 1-continued $$\text{(I)}$$

| Example No. | $R^1$ | $R^2$ | $R^3$ | Melting point [°C.] |
|---|---|---|---|---|
| 26 | —CH$_3$ | H | (4-methoxy-6-methyl-pyrimidin-2-yl) | 151 (decomposition) |
| 27 | —CH$_3$ | —CH$_3$ | (4-methoxy-6-methyl-pyrimidin-2-yl) | 135 |
| 28 | —CH$_3$ | H | (6-methyl-pyrimidin-2-yl) | 187 |

Preparation of starting substances of the formula (III)

Example (III-1)

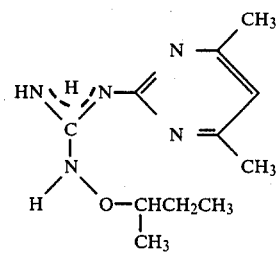

A mixture of 143 g (0.97 mole) of 2-cyanoamino-4,6-dimethyl-pyrimidine, 94 g (1.06 mole) of O-sec.-butyl-hydroxylamine and 190 ml of ethanol is heated at the boiling point under reflux for 6 hours. The mixture is then filtered with suction, the filtrate is concentrated and 500 ml of water are added to the residue. The product thereby obtained as crystals is isolated by filtration with suction.

131 g (57% of theory) of N'-(4,6-dimethyl-pyrimidin-2-yl)-N''-sec.-butoxy-guanidine of melting point 78° C. are obtained.

The compounds of the formula (III) listed in the following Table 2 can be prepared analogously:

TABLE 2

$$\text{(III)}$$

| Example No. | $R^1$ | $R^2$ | $R^3$ | Melting point [°C.] |
|---|---|---|---|---|
| III-2 | —CH$_2$CH(CH$_3$)$_2$ | H | (4,6-dimethyl-pyrimidin-2-yl) | 52 |

TABLE 2-continued $$\underset{NH}{\overset{R^1O}{\underset{HN}{\vphantom{X}}}}C-N\overset{R^2}{\underset{R^3}{\vphantom{X}}} \quad (III)$$

| Example No. | R¹ | R² | R³ | Melting point [°C.] |
|---|---|---|---|---|
| III-3 | $-CH_2CH=CH_2$ | H | 4,6-dimethylpyrimidin-2-yl | 103 |
| III-4 | $-CH(CH_3)_2$ | H | 4,6-dimethylpyrimidin-2-yl | 84 |
| III-5 | $-CH_2-CH_2-C_6H_5$ | H | 4,6-dimethylpyrimidin-2-yl | $n_D^{24} = 1.5776$ |
| III-6 | $-C_4H_9(-n)$ | H | 4,6-dimethylpyrimidin-2-yl | (Oil) |
| III-7 | $-C_8H_{17}(-n)$ | H | 4,6-dimethylpyrimidin-2-yl | 58 |
| III-8 | $-CH_2-(2-chlorophenyl)$ | H | 4,6-dimethylpyrimidin-2-yl | 102–103 |
| III-9 | $-CH_2CH_2CH_2Cl$ | H | 4,6-dimethylpyrimidin-2-yl | 137 |
| III-10 | $-C_6H_5$ | H | 4,6-dimethylpyrimidin-2-yl | 189–192 (decomposition) |

TABLE 2-continued $$\underset{NH}{\overset{R^1O}{\underset{HN}{\bigvee}}}C-N\underset{R^3}{\overset{R^2}{\bigvee}} \quad (III)$$

| Example No. | R¹ | R² | R³ | Melting point [°C.] |
|---|---|---|---|---|
| III-11 | —CH₂COOCH₃ | H | 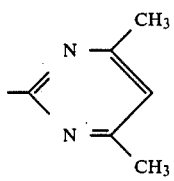 | 148–149 |
| III-12 | —CH₂COOC₂H₅ | H | 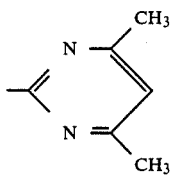 | 98–99 |
| III-13 | —CH(CH₃)—COOCH₃ | H | 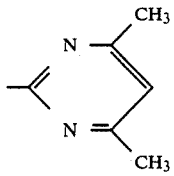 | 147–148 |
| III-14 | —CH₂—C₆H₄—CH₃ | H | 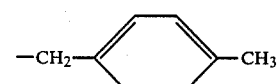 | 85–86 |
| III-15 | —CH₂—(2-F-C₆H₄) | H | 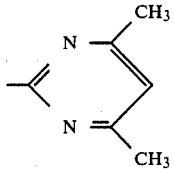 | 114 |
| III-16 | cyclohexyl | H | 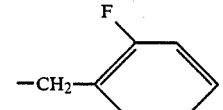 | |
| III-17 | —CH₂-cyclohexyl | H | 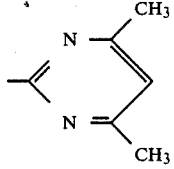 | | where R³ in each case is:

$$\underset{N}{\overset{CH_3}{\bigvee}}\!\!=\!\!\underset{N}{\overset{}{\bigvee}}\!\!=\!\!\underset{CH_3}{\overset{}{\bigvee}}$$

TABLE 2-continued $$\underset{NH}{\overset{R^1O}{\underset{HN}{\bigvee}}}C-N\underset{R^3}{\overset{R^2}{\bigvee}} \quad (III)$$

| Example No. | R¹ | R² | R³ | Melting point [°C.] |
|---|---|---|---|---|
| III-18 | —CH₂CON(CH₃)₂ | H | (4,6-dimethylpyrimidin-2-yl) | |
| III-19 | —CH₂OCH₃ | H | (4,6-dimethylpyrimidin-2-yl) | |
| III-20 | —CH₂SCH₃ | H | (4,6-dimethylpyrimidin-2-yl) | |
| III-21 | —CH₂—C₆H₄—COOC₂H₅ (para) | H | (4,6-dimethylpyrimidin-2-yl) | 138 |
| III-22 | —CH₂CF₃ | H | (4,6-dimethylpyrimidin-2-yl) | |
| III-23 | —CH₂—(2,6-dichlorophenyl) | H | (4,6-dimethylpyrimidin-2-yl) | 140–145 |
| III-24 | —CH₂—C₆H₄—NO₂ (para) | H | (4,6-dimethylpyrimidin-2-yl) | 170 |
| III-25 | —CH₃ | H | (4,6-dimethylpyrimidin-2-yl) | 134–136 |

TABLE 2-continued $$\text{(III)} \quad \underset{NH}{\overset{R^1O}{\underset{HN}{\overset{|}{\text{N}}}}}C-N\overset{R^2}{\underset{R^3}{}}$$

| Example No. | R¹ | R² | R³ | Melting point [°C.] |
|---|---|---|---|---|
| III-26 | —C₂H₅ | H | [pyrimidinyl with 4,6-diCH₃] | 88 |
| III-27 | —CH₂—C₆H₅ | H | [pyrimidinyl with 4,6-diCH₃] | 102 |
| III-28 | —CH₃ | —CH₃ | [pyrimidinyl with 4,6-diCH₃] | 95 |
| III-29 | —CH₃ | —CH₃ | [pyrimidinyl with 4,6-diOCH₃] | 135 |
| III-30 | —CH₃ | H | [pyrimidinyl with 4,6-diOCH₃] | 122 |
| III-31 | —CH₃ | H | [pyrimidinyl with 4-CH₃] | 152 |
| III-32 | —CH₃ | H | [pyrimidinyl with 4-OCH₃, 6-CH₃] | 126 |
| III-33 | —CH₃ | H | [pyridinyl with CH₃ groups] | 110 |

TABLE 2-continued $$\text{(III)} \quad \underset{NH}{\overset{R^1O}{\underset{HN}{\big|}}}C-N\overset{R^2}{\underset{R^3}{\big\langle}}$$

| Example No. | $R^1$ | $R^2$ | $R^3$ | Melting point [°C.] |
|---|---|---|---|---|
| III-34 | —CH$_3$ | H | (4-methyl-6-difluoromethoxy-pyrimidin-2-yl) | |
| III-35 | —C$_2$H$_5$ | H | (4-methyl-6-ethoxy-pyrimidin-2-yl) | |
| III-36 | —C$_4$H$_9$(—sec.) | H | (4,6-dimethoxy-pyrimidin-2-yl) | 68 |
| III-37 | —C$_4$H$_9$(—i) | H | (4,6-dimethoxy-pyrimidin-2-yl) | 76 |
| III-38 | —CH$_3$ | H | (4-ethyl-pyrimidin-2-yl) | 98 |
| III-39 | —C$_3$H$_7$(—n) | H | (4,6-dimethyl-pyrimidin-2-yl) | 54 |
| III-40 | —CH$_2$—COOC$_3$H$_7$(—i) | H | (4,6-dimethyl-pyrimidin-2-yl) | 112 |
| III-41 | —C$_2$H$_5$ | H | (4-ethyl-pyrimidin-2-yl) | |

TABLE 2-continued $$\begin{array}{c} R^1O \\ | \\ HN \\ \diagdown \\ C-N \diagup R^2 \\ \diagup \\ NH \end{array} \diagdown R^3 \qquad (III)$$

| Example No. | R¹ | R² | R³ | Melting point [°C.] |
|---|---|---|---|---|
| III-42 | —CH₂—C₆H₅ (benzyl) | H | 2-(4-methylpyrimidinyl) | 150 |
| III-43 | —CH₂—(2-chlorophenyl) | H | 2-(4-methylpyrimidinyl) | 140 |
| III-44 | —C₂H₅ | H | 2-(4-methylpyrimidinyl) | 95 |
| III-45 | —CH₂—(2-fluorophenyl) | H | 2-(4-methylpyrimidinyl) | 205 |
| III-46 | —CH₂CH₂CH₂—Cl | H | 2-(4-methylpyrimidinyl) | 102 |
| III-47 | —CH₂—COOC₂H₅ | H | 2-(4-methylpyrimidinyl) | |
| III-48 | —CH₂—CH=CH₂ | H | 2-(4-methylpyrimidinyl) | |
| III-49 | —C₄H₉(—n) | H | 2-(4-methylpyrimidinyl) | |
| III-50 | —C₄H₉(—sec.) | H | 2-(4-methylpyrimidinyl) | |

TABLE 2-continued $$\underset{NH}{\overset{R^1O}{\underset{HN}{\diagdown}}}C-N\underset{R^3}{\overset{R^2}{\diagup}} \quad (III)$$

| Example No. | $R^1$ | $R^2$ | $R^3$ | Melting point [°C.] |
|---|---|---|---|---|
| III-51 | —CH₃ | H | pyrimidinyl (4-OCH₃, 6-Cl) | 112 |
| III-52 | —CH₂—C₆H₅ | H | pyrimidinyl (4-OCH₃, 6-Cl) | |
| III-53 | —CH₃ | H | pyrimidinyl (4-CH₃, 6-CH₃) | 143 |
| III-54 | —CH₂—C₆H₅ | H | pyrimidinyl (4-OCH₃, 6-OCH₃) | 74 |
| III-55 | —CH₃ | H | pyrimidinyl | 107–109 |
| III-56 | —CH₃ | H | pyrimidinyl (4-OC₂H₅, 6-OC₂H₅) | |
| III-57 | —CH₂—C₆H₅ | H | pyrimidinyl (4-CH₃, 6-OCH₃) | $n_D^{20} = 1.5645$ |
| III-58 | —CH₂—C₆H₅ | H | pyrimidinyl (4-C₂H₅) | 112 |

TABLE 2-continued $$
\underset{NH}{\overset{R^1O}{\underset{|}{HN}}}C-N\underset{R^3}{\overset{R^2}{}}
\qquad (III)
$$

| Example No. | R¹ | R² | R³ | Melting point [°C.] |
|---|---|---|---|---|
| III-59 | —CH₂CH₂CH₂CH₂Cl | H | (4,6-dimethylpyrimidin-2-yl) | amorphous |
| III-60 | —CH₂CH₂Cl | H | (4,6-dimethylpyrimidin-2-yl) | amorphous |
| III-61 | —CH[C₆H₅]₂ | H | (4-methylpyrimidin-2-yl) | 165 |
| III-62 | —CH₂—CH=CHCl | H | (4,6-dimethylpyrimidin-2-yl) | — |

Preparation of the starting substances of the formula (IV)

Example (IV-1)

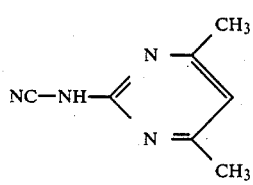

(Process (b))

A mixture of 42 g (0.5 mole) of cyanoguanidine ("dicyandiamide") and 50 g (0.5 mole) of 2,4-pentanedione ("acetylacetone") is heated at 120° C. for 15 hours. After the reaction mixture has cooled, 500 ml of water are then added and the solution is acidified with hydrochloric acid at 0° C. to 10° C. The product thereby obtained as crystals is isolated by filtration with suction.

51.8 g (70% of theory) of 2-cyanoamino-4,6-dimethylpyrimidine of melting point 205° C. are obtained.

Example (IV-2)

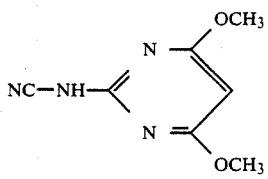

(Process (c))

A solution, heated to 100° C., of 24 g (0.427 mole) of potassium hydroxide in 100 ml of water is added to a mixture of 9.2 g (0.043 mole) of N-(4,6-dimethoxypyrimidin-2-yl)-thiourea and 70 ml of water at 100° C., with stirring. The mixture is subsequently stirred at 100° C. for 2 minutes and a solution, warmed to 100°, of 16.2 g (0.05 mole) of lead-II acetate in 30 ml of water is added. The mixture is heated under reflux for a further 5 minutes and then cooled to 0° C. to 5° C., and 30 ml of glacial acetic acid are added to the aqueous solution. The product thereby obtained as crystals is isolated by filtration with suction.

6.3 g (81.5% of theory) of 2-cyanoamino-4,6-dimethoxy-pyrimidine of melting point 202° C. are obtained.

The same result is obtained if the reaction is carried out in water/methanol mixtures under otherwise identical conditions.

The compounds of the formula (IV) listed in the following Table 3 can be prepared by the process described by way of example in the preceding examples:

TABLE 3

$$N\equiv C-N\begin{matrix}R^2\\R^3\end{matrix} \quad (IV)$$

| Example No. | $R^2$ | $R^3$ | Melting point [°C.] |
|---|---|---|---|
| IV-3 | H | 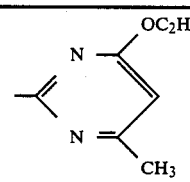 | |
| IV-4 | H | 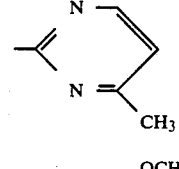 | 203 |
| IV-5 | H | 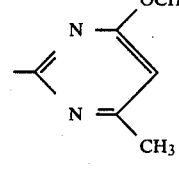 | 258 |
| IV-6 | H | 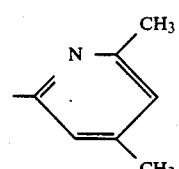 | 221 |
| IV-7 | H | 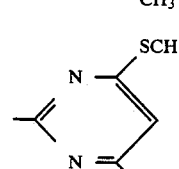 | |
| IV-8 | H | 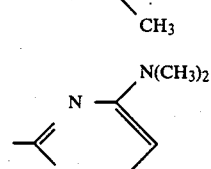 | |
| IV-9 | H | 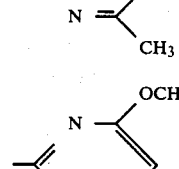 | 174 |
| IV-10 | H | 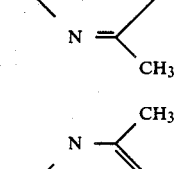 | 174 |

TABLE 3-continued $$N\equiv C-N\begin{matrix}R^2\\R^3\end{matrix} \quad (IV)$$

| Example No. | $R^2$ | $R^3$ | Melting point [°C.] |
|---|---|---|---|
| IV-11 | H | 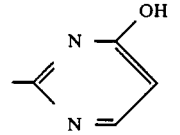 | >300 |
| IV-12 | H | 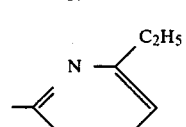 | 146 |
| IV-13 | H | 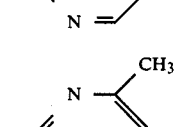 | 126 |
| IV-14 | H | 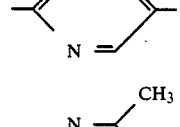 | 234 |
| IV-15 | H | 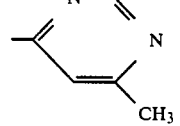 | 200 |
| IV-16 | H | 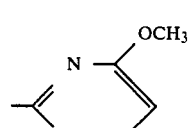 | |
| IV-17 | H | 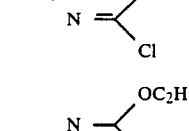 | |
| IV-18 | H | 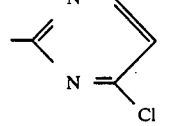 | 247–250 |
| IV-19 | H | 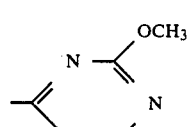 | |

TABLE 3-continued $$N\equiv C-N\begin{matrix}R^2\\ \\R^3\end{matrix} \quad (IV)$$

| Example No. | R² | R³ | Melting point [°C.] |
|---|---|---|---|
| IV-20 | H | 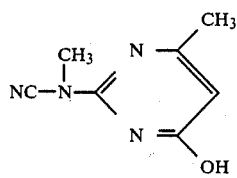 | 186 |
| IV-21 | H | 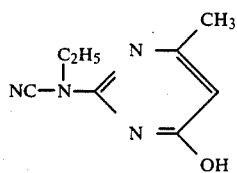 | |

2-(Alkyl-cyano-amino)-pyrimidines of the formula (IV) can be prepared, for example, as follows:

Example (IV-22)

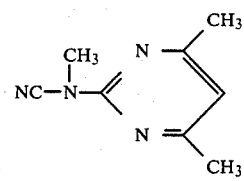

12.6 g (0.1 mole) of dimethyl sulphate are added dropwise to a solution of 15 g (0.1 mole) of 2-cyanoamino-4-hydroxy-6-methyl-pyrimidine—prepared according to process (b)—and 4.1 g (0.1 mole) of sodium hydroxide in 60 ml of water, whereupon the reaction temperature rises from 20° C. to 40° C. After the mixture has been stirred at 20° C. for two hours, the product, which is obtained as crystals, is isolated by filtration with suction.

11.1 g (68% of theory) of 2-(methyl-cyano-amino)-4-hydroxy-6-methyl-pyrimidine of melting point 290° C. are obtained.

The following compound is obtained analogously:

Example (IV-23)

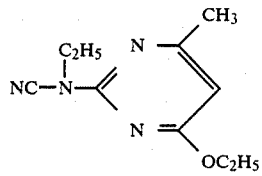

Melting point: 215° C. to 220° C.

Example (IV-24)

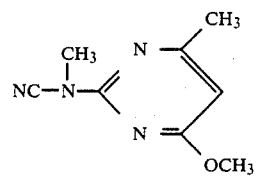

127.5 g (1 mole) of dimethyl sulphate are added dropwise to a solution of 75 g (0.5 mole) of 2-cyanoamino-4-hydroxy-6-methyl-pyrimidine—prepared according to process (b)—and 44 g (1.1 moles) of sodium hydroxide in 750 ml of water, whereupon the reaction temperature rises from 20° C. to 35° C. After the mixture has been stirred at 20° C. for twelve hours, the pH value is brought to between 9 and 10 by addition of sodium hydroxide solution and the product obtained as crystals is isolated by filtration with suction.

13 g (15% of theory) of 2-(methyl-cyano-amino)-4-methoxy-6-methyl-pyrimidine of melting point 123° C. are obtained.

The following compounds are obtained analogously:

Example (IV-25)

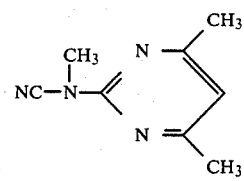

Melting point: 104° C.

Example (IV-26)

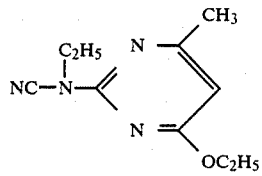

Melting point: 71° C.

Preparation of the starting substances of the formula (X)

Example (X-1)

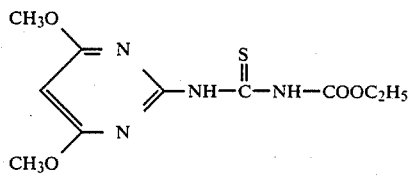

A mixture of 15.5 g (0.1 mole) of 2-amino-4,6-dimethoxy-pyrimidine, 13.1 g (0.1 mole) of ethoxycarbonyl isothiocyanate and 200 ml of acetonitrile is stirred at 60° C. for 2 hours. It is then cooled to 10° C. and the product obtained as crystals is isolated by filtration with suction.

22.5 g (79% of theory) of 1-(ethoxycarbonyl)-3-(4,6-dimethoxy-pyrimidin-2-yl)-thiourea of melting point 194° C. (decomposition) are obtained.

The compounds of the formula (X) listed in the following Table 4 can be prepared by the process described by way of example in the preceding example:

TABLE 4

$$\underset{R^7-\overset{O}{\overset{\|}{C}}-NH-\overset{S}{\overset{\|}{C}}-NH-R^3}{} \quad (X)$$

| Example No. | R⁷ | R³ | Melting point [°C.] |
|---|---|---|---|
| (X-2) | 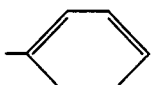 | 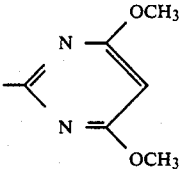 | 189 |
| (X-3) |  | 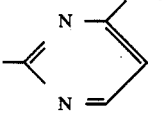 | 198–199 (decomposition) |
| (X-4) | —OC₂H₅ | 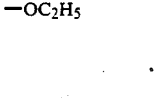 | 217 |
| (X-5) | 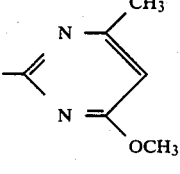 | 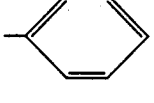 | 190 |
| X-6 | —OC₂H₅ | 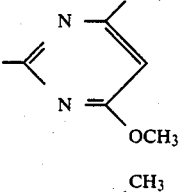 | 140 |
| X-7 | 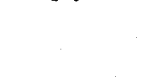 | 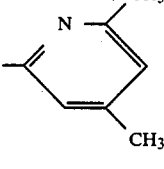 | 145 |
| X-8 |  | 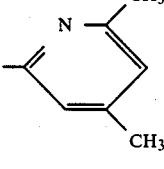 | 161 |
| X-9 | —OC₂H₅ | 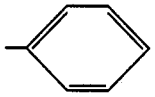 | 119 |
| X-10 | 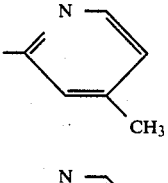 | 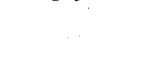 | 182 |
| X-11 | —OC₂H₅ | 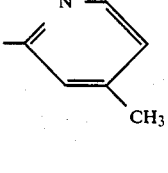 | 184–185 |
| X-12 | —OC₂H₅ | 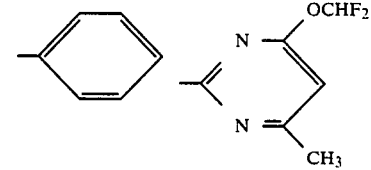 | 173 |
| X-13 | —OC₂H₅ | 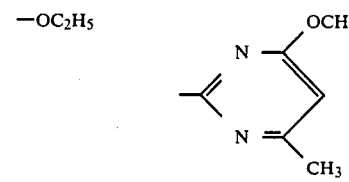 | 160–162 |
| X-14 | —OC₂H₅ | 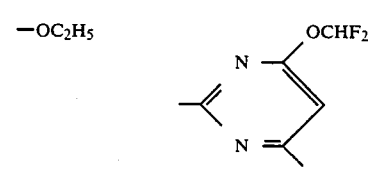 | 169 |
| X-15 | —OC₂H₅ | 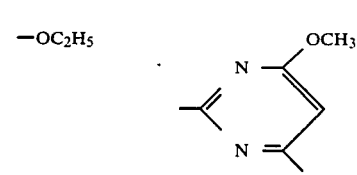 | |
| X-16 | —OC₂H₅ | 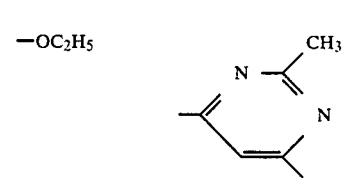 | 168 |
| X-17 | 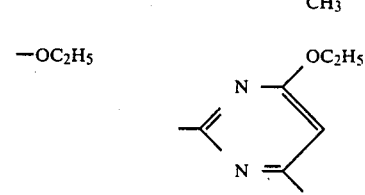 | 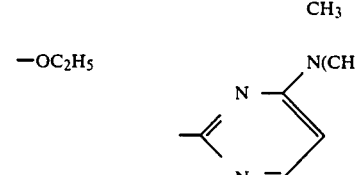 | 173 |

TABLE 4-continued $$R^7-\overset{O}{\underset{\|}{C}}-NH-\overset{S}{\underset{\|}{C}}-NH-R^3 \quad (X)$$

| Example No. | R⁷ | R³ | Melting point [°C.] |
|---|---|---|---|
| X-18 | (phenyl) | 4,6-bis(OC₂H₅)-pyrimidin-2-yl | 179 |
| X-19 | —OC₂H₅ | 4,6-bis(OC₂H₅)-pyrimidin-2-yl | 159 |
| X-20 | (phenyl) | 4-CH₃-6-OC₂H₅-pyrimidin-2-yl | 156 |

Preparation of the starting substances of the formula (XI)

Example (XI-1)

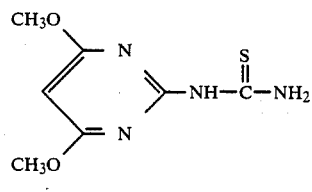

A mixture of 5.0 g (0.0175 mole) of 1-(ethoxycarbonyl)-3-(4,6-dimethoxy-pyrimidin-2-yl)-thiourea, 4.0 g (0.1 mole) of sodium hydroxide and 100 ml of water is stirred at 20° C. for 2 days. Dilute hydrochloric acid is then added dropwise, with stirring, until the solution has been rendered acid and the evolution of $CO_2$ has ended. The product obtained as crystals is isolated by filtration with suction.

3.5 g (94% of theory) of 4,6-dimethoxy-pyrimidin-2-yl-thiourea of melting point 245°–248° C. (decomposition) are obtained.

The compounds of the formula (XI) listed in the following Table 5 can be prepared by the process described by way of example in the preceding example:

TABLE 5

$$H_2N-\overset{S}{\underset{\|}{C}}-NH-R^3 \quad (XI)$$

| Example No. | R³ | Melting point [°C.] |
|---|---|---|
| XI-2 | 4-CH₃-pyrimidin-2-yl | 264–265 |
| XI-3 | 4-CH₃-6-OCH₃-pyrimidin-2-yl | 207 |
| XI-4 | 4,6-di-CH₃-pyrimidin-2-yl | 260 |
| XI-5 | 4-CH₃-pyridin-2-yl | 214–215 |
| XI-6 | 4-OCHF₂-6-CH₃-pyrimidin-2-yl | 192–194 |
| XI-7 | 4-OCH₃-6-Cl-pyrimidin-2-yl | 225–227 (decomposition) |
| XI-8 | 4,6-di-CH₃-pyridin-2-yl | 248 |
| XI-9 | 4-N(CH₃)₂-6-Cl-pyrimidin-2-yl | |

TABLE 5-continued

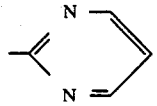

| Example No. | $R^3$ | Melting point [°C.] |
|---|---|---|
| XI-10 | (pyrazinyl group) | 263 |

Example A

Pre-emergence test/Greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the following compound of the preparation examples (1) exhibited a very good action in combating monocotyledon and dicotyledon weeds.

Example B

Post-emergence test/Greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the following compound of the preparation examples (1) exhibited a very good activity in combating monocotyledon and dicotyledon weeds.

We claim:

1. A process for the preparation of a benzodisultam of the formula

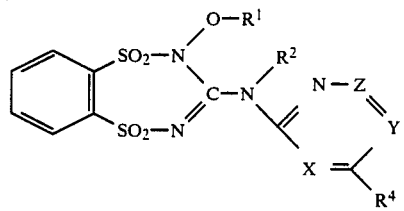

in which $R^1$ represents $C_1$–$C_{12}$-alkyl which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-amino-carbonyl; or represents $C_3$–$C_6$-alkenyl which is optionally substituted by fluorine, chlorine or bromine; or represents $C_3$–$C_6$-alkinyl, $C_3$–$C_6$-cycloalkyl, $C_3$–$C_6$-cycloalkyl-$C_1$–$C_2$-alkyl or phenyl-$C_1$–$C_2$-alkyl which is optionally substituted by fluorine, chlorine, nitro, cyano, $C_1$–$C_4$-alkyl, $C_1$–$C_4$-alkoxy or $C_1$–$C_4$-alkoxy-carbonyl; or represents phenyl which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxycarbonyl;

$R^2$ represents hydrogen; $C_1$–$C_4$-alkyl which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-aminocarbonyl; or represents $C_3$–$C_6$-alkenyl, $C_3$–$C_6$-alkinyl or phenyl-$C_1$–$C_2$-alkyl which is optionally substituted by fluorine, chlorine, nitro, cyano, $C_1$–$C_4$-alkyl, $C_1$–$C_4$-alkoxy or $C_1$–$C_4$-alkoxy-carbonyl; $R^4$ represents hydrogen; fluorine, chlorine; bromine, hydroxyl; $C_1$–$C_4$-alkyl which is optionally substituted by fluorine and/or chlorine; $C_1$–$C_4$-alkoxy which is optionally substituted by fluorine and/or chlorine; $C_1$–$C_4$-alkylthio which is optionally substituted by fluorine and/or chlorine; amino, $C_1$–$C_4$-alkylamino or di-($C_1$–$C_4$-alkyl)-amino;

X represents nitrogen or a methine bridge (CH),
Y represents nitrogen or an optionally substituted methine bridge C-$R^5$,
$R^5$ represents hydrogen, fluorine, chlorine, bromine, $C_1$–$C_4$-alkyl, $C_1$–$C_4$-alkylcarbonyl or $C_1$–$C_4$-alkoxycarbonyl,
Z represents nitrogen or an optionally substituted methine bridge C-$R^6$,
$R^6$ represents hydrogen; fluorine; chlorine; bromine; hydroxyl; $C_1$–$C_4$-alkyl which is optionally substituted by fluorine and/or chlorine; $C_1$–$C_4$-alkoxy which is optionally substituted by fluorine and/or chlorine; $C_1$–$C_4$-alkylthio which is optionally substituted by fluorine and/or chlorine; amino; $C_1$–$C_4$-alkylamino or di-$C_1$–$C_4$-alkyl)-amino comprising reacting benzene-1,2-disulphonic acid dichloride of the formula

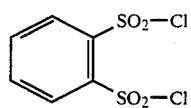
with an oxyguanidine derivative of the formula
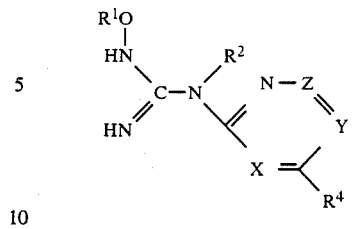
in the presence of an acid acceptor.
* * * * *

UNITED STATES PATENT AND TRADEMARK OFFICE
CERTIFICATE OF CORRECTION

PATENT NO. : 4,769,455

DATED : September 6, 1988

INVENTOR(S) : Hans-Joachim Diehr, et al

It is certified that error appears in the above-identified patent and that said Letters Patent is hereby corrected as shown below:

| | |
|---|---|
| Col. 1, line 66 | Delete "$c_4$" and substitute --$C_4$-- |
| Col. 4, line 3 | After "4" insert -- - -- |
| Col. 4, line 13 | End of line delete "-N--" and substitute -- -N"- -- |
| Col. 4, line 42 | Delete "Ti" |

Signed and Sealed this

Twenty-eighth Day of March, 1989

Attest:

DONALD J. QUIGG

*Attesting Officer*      *Commissioner of Patents and Trademarks*